US008080003B1

(12) United States Patent
Burton et al.

(10) Patent No.: US 8,080,003 B1
(45) Date of Patent: *Dec. 20, 2011

(54) METHOD AND IMPLANTABLE APPARATUS FOR THE INTRA-OSSEAL MONITORING OF BIOLOGICAL SUBSTANCES IN THE BONE MARROW

(75) Inventors: Charles Victor Burton, St. Paul, MN (US); Robert Harold Lovett, Savage, MN (US)

(73) Assignee: Paunceforte Technologies, LLC, Shakopee, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/868,329

(22) Filed: Aug. 25, 2010

Related U.S. Application Data

(63) Continuation-in-part of application No. 12/775,111, filed on May 6, 2010, now abandoned, which is a continuation-in-part of application No. 11/656,341, filed on Jan. 22, 2007, now Pat. No. 7,753,903.

(60) Provisional application No. 60/764,854, filed on Feb. 2, 2006.

(51) Int. Cl.
*A61K 9/22* (2006.01)

(52) U.S. Cl. .................. 604/891.1; 600/309; 600/316; 600/365; 604/66

(58) Field of Classification Search ........... 600/309–344
See application file for complete search history.

(56) References Cited

U.S. PATENT DOCUMENTS

| 5,305,745 | A | | 4/1994 | Zacouto |
| 5,357,974 | A | | 10/1994 | Baldridge |
| 5,960,797 | A | * | 10/1999 | Kramer et al. ............... 128/899 |
| 2004/0193025 | A1 | | 9/2004 | Steil et al. |
| 2010/0145317 | A1 | * | 6/2010 | Laster et al. ............... 604/891.1 |

* cited by examiner

*Primary Examiner* — Eric Winakur
*Assistant Examiner* — Marjan Fardanesh
(74) *Attorney, Agent, or Firm* — Westman, Champlin & Kelly, P.A.; Z. Peter Sawicki

(57) ABSTRACT

A method for monitoring and controlling biological substances found in the bloodstream include implanting in-vivo a pedestal such that a sensor mounted on the pedestal extends into the bone marrow for sensing the biological substance. A transmitter is included for transmitting signals from the sensor to a receiver. An apparatus that includes a monitoring device and a drug delivery device and components to communicate between the monitoring and drug delivery devices.

10 Claims, 5 Drawing Sheets

METHOD AND IMPLANTABLE APPARATUS FOR THE INTRA-OSSEAL MONITORING OF BIOLOGICAL SUBSTANCES IN THE BONE MARROW

CROSS REFERENCE TO RELATED APPLICATION(S)

The present application is a continuation-in-part of and claims priority of U.S. patent application Ser. No. 12/775,111, filed May 6, 2010 which is a continuation-in-part of application Ser. No. 11/656,341, filed Jan. 22, 2007, now U.S. Pat. No. 7,753,903, granted Jul. 13, 2010 which claims priority from Provisional Application No. 60/764,854, filed on Feb. 2, 2006, which is hereby incorporated by reference in its entirety.

FIELD OF THE INVENTION

The present invention relates to an implantable device for the testing for, and the delivery of substances into, the intra-osseal space within a mammal, particularly in a human being, to monitor biological substances in the intra-osseal space which is similar to the blood stream, particularly for the determination of glucose content, the delivery of drugs, particularly insulin into the intra-osseal bone marrow, and the integration of the foregoing, as well as related and ancillary matters and the methods respecting the foregoing.

BACKGROUND OF THE INVENTION

Currently, there are a large number of methods and devices designed to detect blood glucose levels and particularly hypoglycemia in human beings with diabetes mellitus. The traditional method for monitoring glucose levels is by "finger sticking" and measuring the glucose level from the blood expressed. Avoiding the pain and discomfort of "finger sticking" has promoted the development of the non-invasive techniques such as measuring glucose concentration using the absorption of light in the infrared spectrum. Another approach has been subcutaneous fluid testing using either a disposable subcutaneous glucose monitor or the relatively permanent implantation of glucose sensors. Additionally, a noninvasive method has been developed in which impedance spectroscopy or similar methods are used to measure glucose concentrations. These various methods and devices have suffered in the reliability of the test results and the survivability of the devices. The most accurate present means of repeatedly and accurately monitoring blood substances is by an indwelling intravascular catheter. The problem with these is that their useful time is limited by tissue breakdown and infection.

SUMMARY OF THE INVENTION

The present invention relates to the development of a stable and reliable implanted device designed to utilize the intra-osseal bone marrow for the chronic and long-term testing for, and delivery of substances into this body compartment within a mammal, particularly in a human being, to monitor biological substances in the blood stream, particularly the level of glucose, and the delivery of drugs, particularly insulin into this compartment as well as the integration of the foregoing, and related and ancillary matters and the methods respecting the foregoing.

In a first aspect, the present invention includes a method for monitoring and controlling biological substance concentrations in the bloodstream of a patient. The method includes implanting in-vivo a monitoring device comprising a pedestal and a sensor such that the sensor mounted on the pedestal extends into bone marrow for sensing the biological substance concentration. The method also includes sensing the concentration of biological substance in the bloodstream with the sensor, implanting in-vivo a drug delivery device into the bone marrow, transmitting signals from the sensor to a receiver relating to the biological substance concentration in the bloodstream and transmitting signals from the receiver to the drug delivery device such that a dose of a drug is administered to the bone marrow of the patient to control the biological substance concentration in the bloodstream. In preferred embodiments, the biological substance is glucose and the drug delivered is insulin.

In a further aspect, the present invention includes an apparatus for monitoring and controlling biological substance concentrations in a bloodstream. The apparatus includes a monitoring device comprising a pedestal and a sensor for implantation into a human body. The sensor is mounted within the pedestal when implanted into a patient and the sensor extends through the bone into bone marrow and is capable of detecting the concentration of a biological substance and transmitting signals that correlate to the concentration of the biological substance in the blood stream. The apparatus also includes a receiver in communication with the sensor wherein the sensor relates information relating to the biological substance concentration in the bloodstream to the receiver and a drug delivery device for implantation into a human body and having a drug delivery end for positioning through the bone and into bone marrow wherein the drug delivery device is in communication with the receiver and delivers a selected dose of a drug into the bone marrow based upon the information received by the receiver from the sensor regarding the biological substance concentration in the bloodstream.

DETAILED DESCRIPTION

The present invention includes an apparatus for the chronic, long-term monitoring and controlling biological substance concentrations in the bloodstream of a patient. The apparatus includes an implantable monitoring device for monitoring the concentration of the biological substance. The monitoring device can utilize the relationship between the bone marrow and the intravascular system with respect to levels of similar substances in the blood stream by implanting a monitoring device having a pedestal and a sensing device into the bone, particularly the iliac crest. Alternatively, the monitoring device may also be placed in other areas with sufficient mass of intra-osseal bone marrow material. An external interrogation device can be used to communicate with the monitoring device.

The present invention also utilizes the reliable relationship between bone marrow and the intravascular system to provide drug delivery into the intra-osseal bone marrow compartment by implanting a drug delivery device into the surrounding bone, particularly the iliac crest, but alternatively in other areas with sufficient mass of bone marrow material and in a manner as to not inhibit the contemporaneous monitoring of levels of substances, particularly glucose or cerebrospinal fluid, in the blood stream.

The present invention includes devices and communication methods that can integrate the monitoring apparatus and the drug delivery apparatus with wired or wireless connections. Methods to monitor the biological substances and deliver the appropriate drugs to control the concentration of the biological substance are also included in the present invention. In particular, methods to monitor the glucose concentration in a patient and delivering the appropriate amounts of insulin in response to the glucose concentration are described herein.

Figure 1:
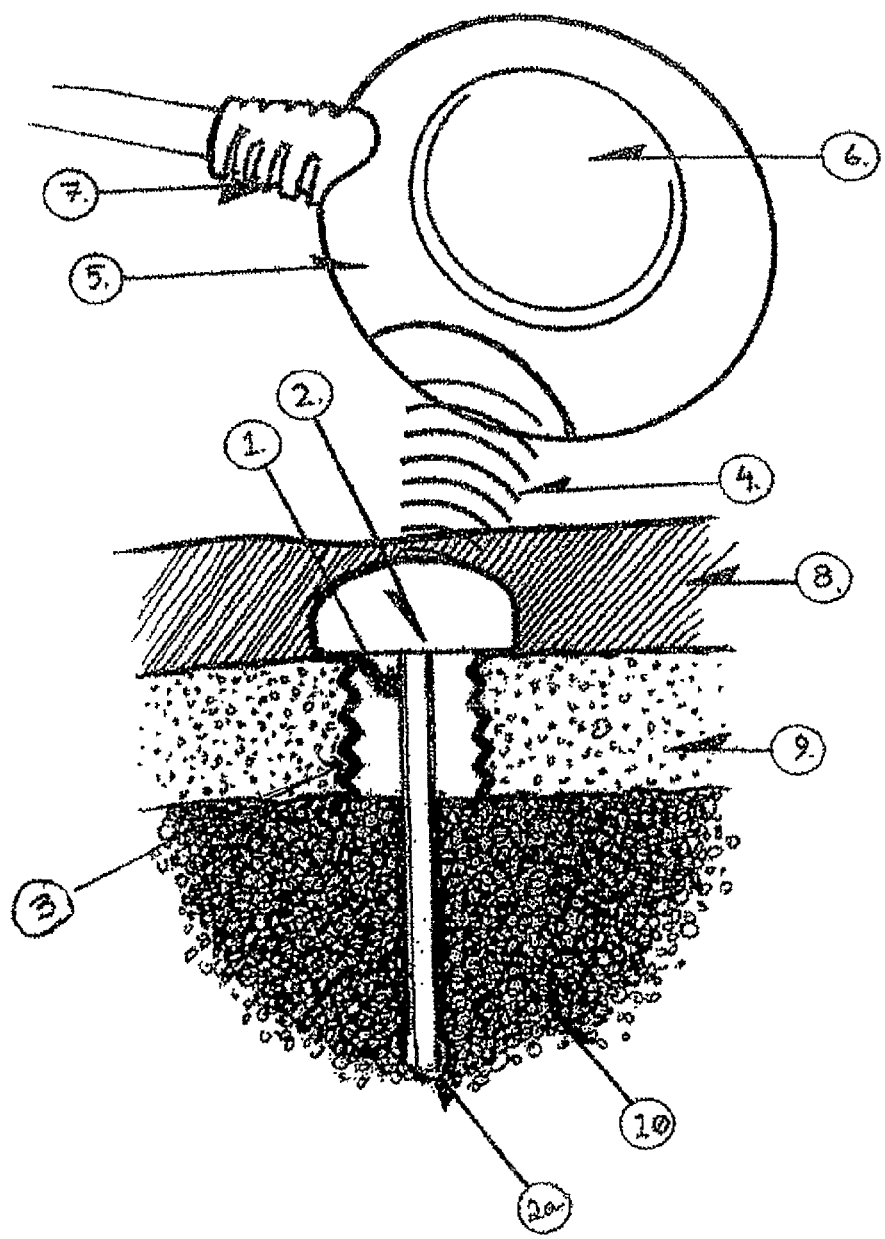
FIG. 1 is a schematic representation of the implanted monitoring device.

FIG. 1 is a schematic representation of the implanted monitoring device 1. In one application, the dermis 8 is populated with conductive material and electrical contact is direct. In another application the electrical contact is indirect (i.e., by radio frequency 4). A sensor 2 acts as a transmitter and receiver. It is either powered with a battery encased in a substance such as titanium or is powered externally be electrical emanations from the external interrogation device 5, which is also the transmitter and receiver 6 of the data generated by the implanted monitoring device 1. The internally placed sensor unit 2 includes a substance sensor end 2a and is implanted in the osseous exterior of the ilium 9 or a site of similar mass with access to a robust supply of blood marrow 10. Monitoring device 1 includes pedestal 3. Pedestal 3 is screwed into the ilium prior to insertion of sensor unit 2. The sensor unit 2 is then screwed into the ilium within threaded pedestal 3. In preferred embodiments, the monitoring device 1 is placed in the posterior iliac crest. The sensor 2 has a geodesic shape to permit interrogation from various angles. The substance sensor end 2a may function by detecting electronic, chemical, or photometric signals. The interrogation phase may be by transmission of radio frequency, infra red light, or other forms of energy transmission 4. A communication link 7 is attached to the interrogation device 5. Communication link 7 may connect to a variety of components including, for example, a implanted power supply, another interrogation device, another transmitter and/or receiver, a drug delivery device.

Figure 2:
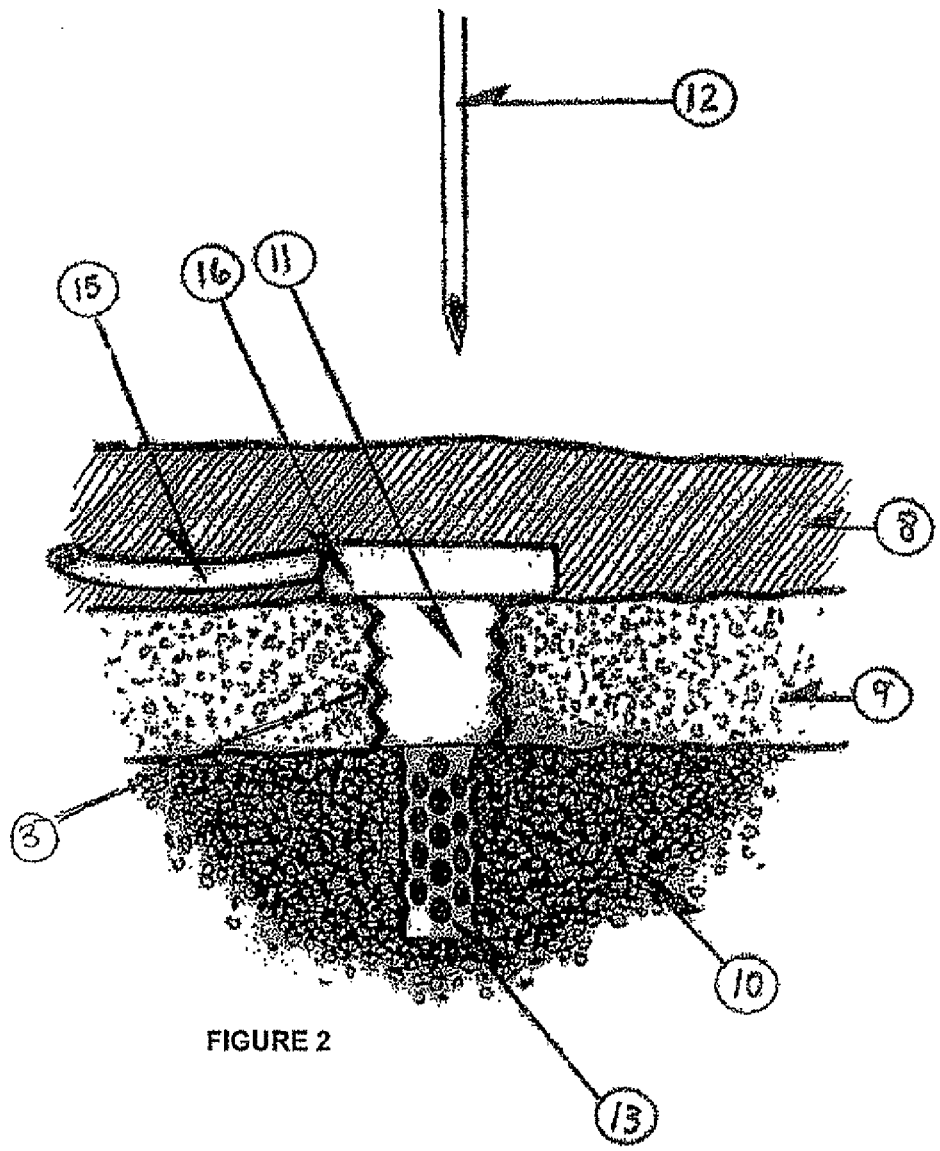
FIG. 2 is a schematic representation of the implanted drug delivery device.

FIG. 2 is a schematic representation of the implanted drug delivery device 11. While the drug delivery device 11 is envisioned to be placed into the ilium 9 or similar osseous site of similar mass and access to a robust supply of blood marrow 10, the drug supply pod could be located remotely. Alternatively, the drug delivery pod may be within the drug delivery device 11.

Drug delivery device 11 includes sensor 16 having perforated end 13 and pedestal 3. Pedestal 3 is screwed into the ilium prior to sensor 16. Sensor 16 is then inserted into the ilium within threaded pedestal 3. Sensor 16 can be a receiver and/or a transmitter. The delivery of the drug could be occasioned by signals sent from the same external device 5 that interrogates monitor 1. A hypodermic needle 12 may optionally be utilized to deliver the drug to the bone marrow through delivery device 11 containing a perforated end 13. The drug is injected into device 11 with a hypodermic needle 12 that is forced through sensor 16 and perforated end 13 to deliver the drug to the bone marrow. An electrical cable 15 is attached to sensor 16. Cable 15 may indicate to interrogation device 5 that the drug has been delivered. Alternatively, sensor 16 may indicate to interrogation device 5 that the drug has been delivered through a wireless connection.

Figure 3:
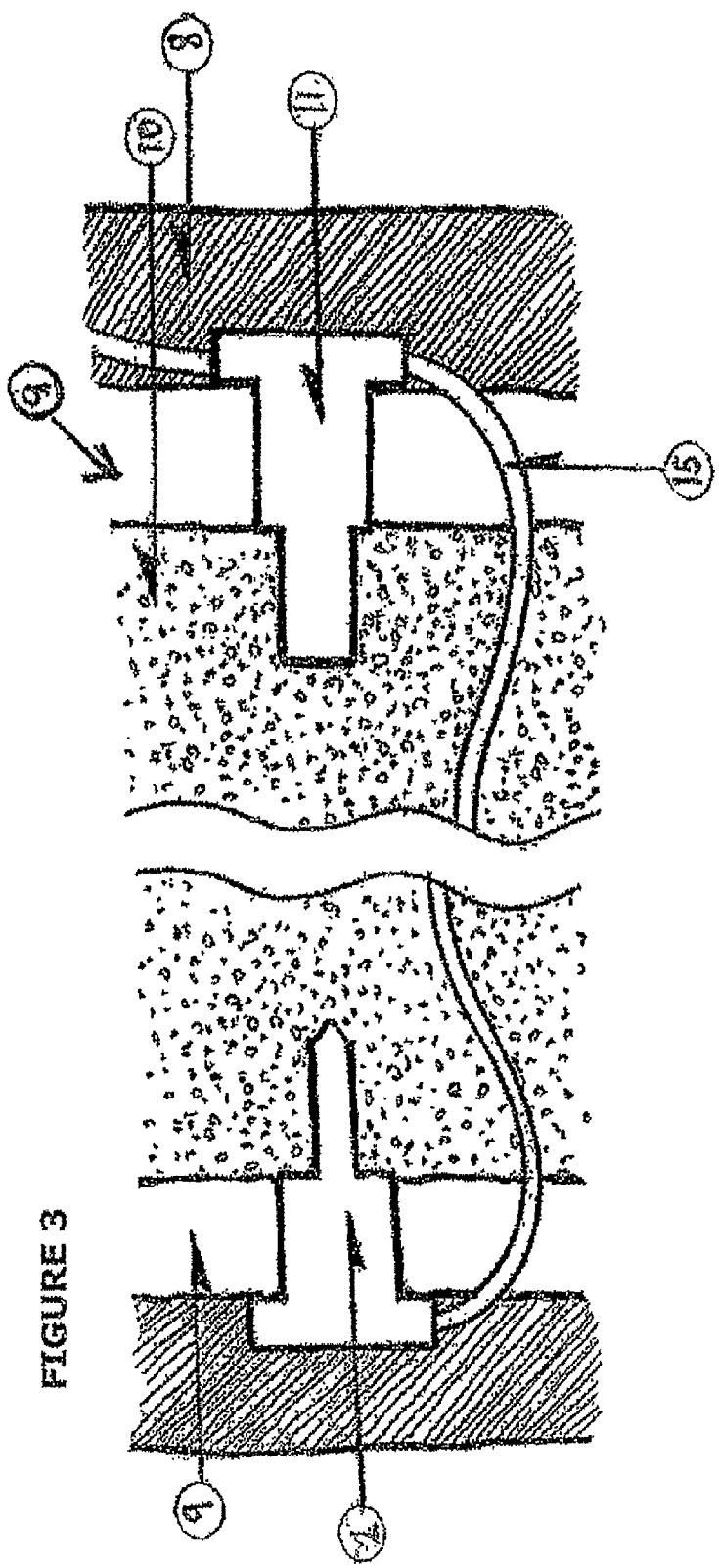
FIG. 3 is a schematic view of the implanted drug delivery device and the drug monitoring device implanted within the body.

FIG. 3 is the preferred embodiment of the integration of the implanted monitoring device 1 and the implanted drug delivery device 11. Here the implanted monitoring device 1 and the implanted drug delivery device 11 are placed on each ilium 9 and communication between the monitoring device and the drug delivery device is through a wired connection 15. Alternatively, the monitoring device and the drug delivery device may communicate through a wireless connection.

Figure 4:
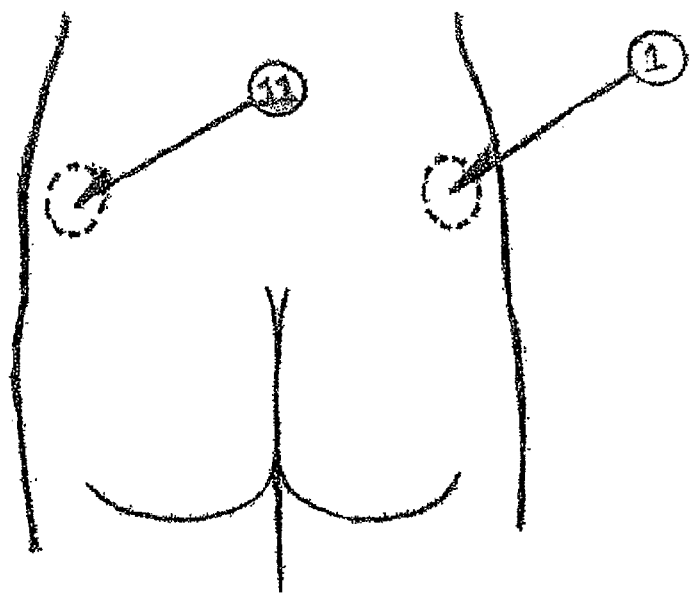
FIG. 4 is a view of the human body illustrating insertion points for the drug delivery device and the monitoring device.

FIG. 4 indicates the preferred location of implantation of monitoring device 1 and drug delivery device 11 on the posterior crest of the ilium. Alternative locations may be appropriate. Additionally, the implanted monitor 1 and drug delivery device 11 could be integrated into a single apparatus or could remain separate but share a proximate location, provided the data generated by the monitor 1 does not become corrupted by the inflow of the substance, such as insulin, delivered by the drug delivery device 11.

Figure 5:
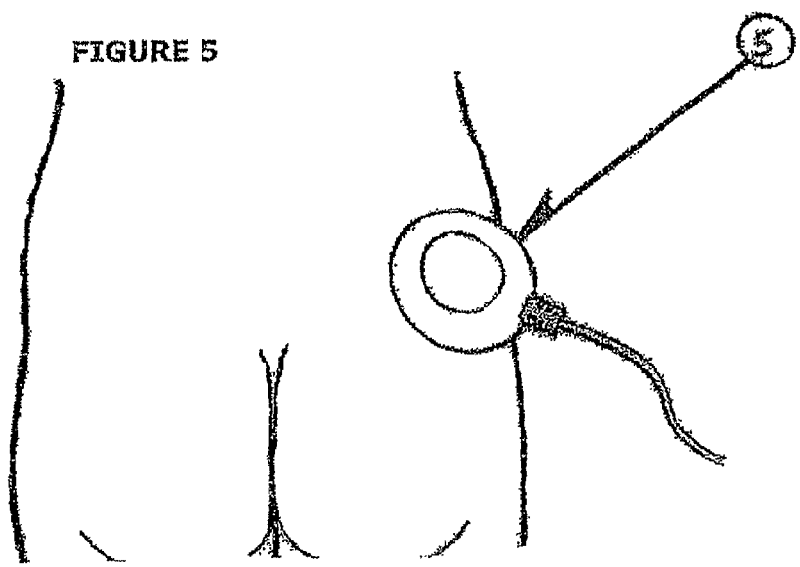
FIG. 5 is a view of the interrogation device placed over the implanted monitoring device.

FIG. 5 indicates the position of the interrogation device 5 placed over the implanted monitor 1 or drug delivery device 11.

Figure 6:
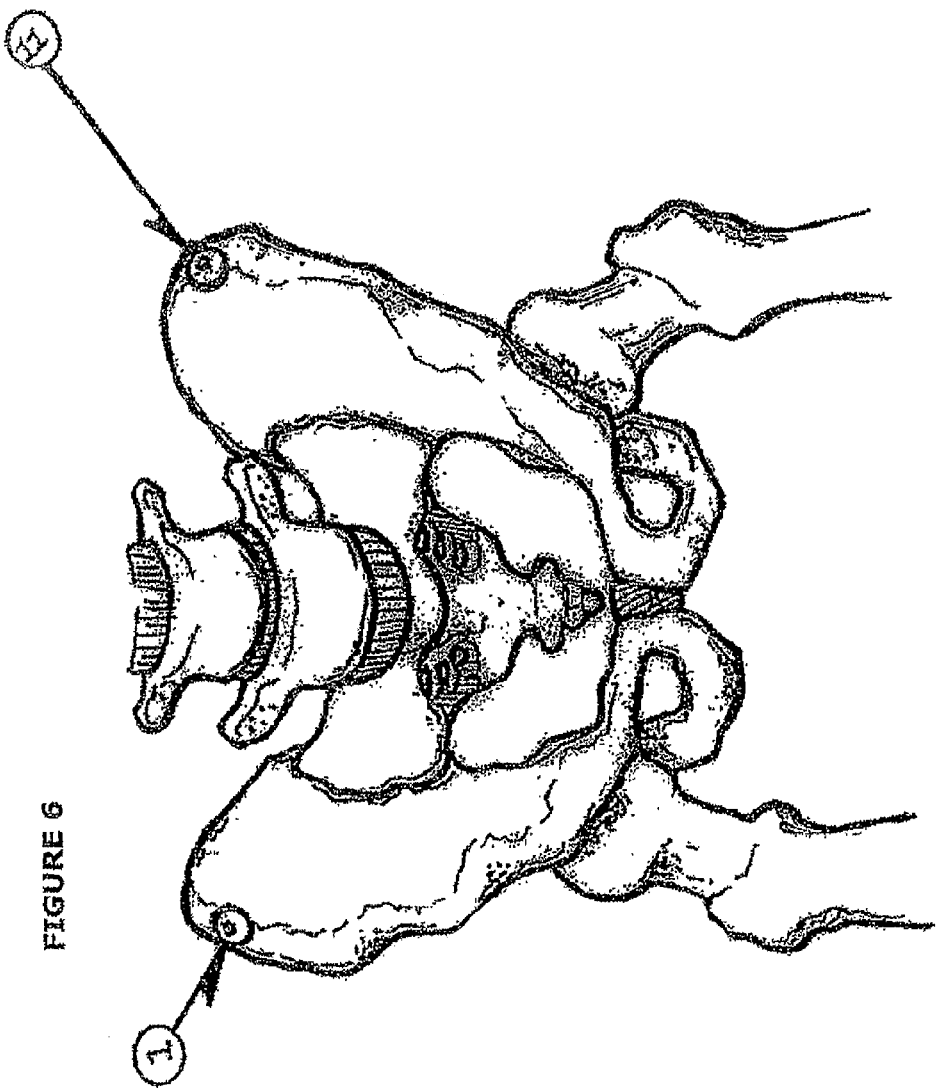
FIG. 6 is a schematic representation of the pelvic bone region of a human body indicating insertion points for the implanted drug monitoring device and the implanted drug delivery device.

FIG. 6 indicates the pelvic bone region of a human body and insertion points, in one exemplary embodiment, for drug monitoring device 1 and drug delivery device 11.

The monitoring devices and the drug delivery devices of the present invention can be placed in a variety of locations. Preferably, these devices are placed in the iliac crest, and more preferably in the posterior iliac crest of a patient. These devices may be placed surgically. However, alternative methods of placing the devices within the patient are also within the scope of this invention. The placement can be performed under supplemented local anesthesia or general anesthesia with the aid of image intensification, image guidance systems and monitors. Preferably, the devices may be placed using minimally invasive procedures using local anesthesia. Additional drugs may be administered to enable or aid in the placement of the devices and/or to comfort the patient. For example, image intensification combined with guidance systems can be used to accurately direct the placement of the devices in the patient.

In one exemplary embodiment, a pedestal screw is first screwed into the pelvic ilium through a small drill hole under bi-plane image intensification control. Three dimensional guidance systems may also be used in addition to bi-plane fluoroscopy. Monitoring may be performed, for example, using fluorescence based monitoring systems. The sensor units can then be inserted through the pedestal. In another exemplary embodiment, the drug monitoring device may be placed in the posterior iliac crest and the drug delivery device may be placed in the contra-lateral posterior iliac crest of the patient. Alternatively, the monitoring device and the drug delivery device may be placed on the same posterior iliac crest. The drug monitoring device and the delivery device may be integrated into a single device.

Communication between the components in the present invention can be using wired or wireless systems. There are a variety of wireless communication systems known such as radio frequency systems and the use of any wireless communication is within the scope of the invention. The monitoring device and the drug delivery device can communicate using wired connections or wireless connections. Communication from the monitoring device to the interrogation device may be wireless as illustrated in FIG. 1. Alternatively, the monitoring device may include a wired connection or a wireless connection that can communicate with the interrogation device or the drug delivery device. For example, the drug delivery device may communicate with the sensor in the monitoring device to indicate the amount of drug that has been delivered. The interrogation device may communicate over a wired or wireless connection with the drug delivery device to indicate that the delivery of the drug should either commence or cease. The implanted devices can be, for example, coordinated and/or optimized by wireless connection to a laptop computer.

The sensors used in the monitoring devices can be based on a variety of methods that are amenable to long-term stability within the marrow of a patient. The methods may employ or detect electronic, chemical or photometric signals. In a preferred embodiment, the sensors are solid state implantable electronic biosensors. These sensors have long-term stability when inserted within the bone marrow of a patient.

The monitoring devices and drug delivery devices described herein can be used to monitor a variety of biological substances and administer a variety of drugs. The drugs administered can be, for example, biological substances normally found in patients. By biological substances is meant substances such as insulin antibiotics, chemotherapeutic agents, analgesics, cerebrospinal fluid (CSF), lymph fluid and the like. The apparatus described herein may also be used to perform a variety of blood work including blood chemistry, blood counts and blood screening for abnormal blood cells such as cancer, sickle cell anemia and the like. In some embodiments, the biological substance monitored is the same as the substance that is administered to control the concentration of the biological substance. In other embodiments, the biological substance monitored can be different from the drug that is administered to control the concentration of the drug. The drug when administered to the patient can cause the concentration of the biological substance to change, thus the drug is administered to change the concentration of the biological substance. For example, in one preferred embodiment, the drug monitored is glucose and the substance administered is insulin.

Although the present invention has been described with reference to preferred embodiments, workers skilled in the art will recognize that changes may be made in form and detail without departing from the spirit and scope of the invention.

What is claimed is:

1. A method for monitoring and controlling biological substance concentrations in the bloodstream of a patient comprising:
   implanting in-vivo a monitoring device comprising a pedestal and a sensor such that the sensor mounted on the pedestal extends into bone marrow for sensing the biological substance concentration;
   sensing the concentration of biological substance in the bloodstream with the sensor;
   implanting in-vivo a drug delivery device into the bone marrow;
   transmitting signals from the sensor to a receiver relating to the biological substance concentration in the bloodstream; and
   transmitting signals from the receiver to the drug delivery device such that a dose of a drug is administered to the bone marrow of the patient to control the biological substance concentration in the bloodstream.

2. The method of claim 1 wherein the monitoring device and the drug delivery device are integrated into a single device.

3. The method of claim 1 wherein the monitoring device and the drug delivery device are spaced apart from each other when implanted.

4. The method of claim 1 wherein the monitoring device and the drug delivery device are implanted in the patient's posterior iliac crest.

5. The method of claim 1 wherein the monitoring device is implanted in the patient's posterior iliac crest and the drug delivery device is implanted in the contra-lateral posterior iliac crest.

6. The method of claim 1 wherein the signals transmitted from the sensor to the receiver are transmitted over a wireless connection.

7. The method of claim 1 wherein the signals transmitted from the sensor to the receiver are transmitted over a wired connection.

8. The method of claim 1 wherein the signals transmitted from the receiver to the drug delivery device are over a wired connection.

9. The method of claim 1 wherein the signals transmitted from the receiver to the drug delivery device are over a wireless connection.

10. The method of claim 1 wherein the biological substance is cerebrospinal fluid.

* * * * *